United States Patent
Orr et al.

(10) Patent No.: US 9,446,210 B2
(45) Date of Patent: Sep. 20, 2016

(54) SYSTEM AND METHOD OF MONITORING BREATHING

(75) Inventors: Joseph Allen Orr, Park City, UT (US); Michael Brian Jaffe, Chesire, CT (US)

(73) Assignee: Koninklijke Philips N.V., Eindhoven (NL)

( * ) Notice: Subject to any disclaimer, the term of this patent is extended or adjusted under 35 U.S.C. 154(b) by 1073 days.

(21) Appl. No.: 13/504,758

(22) PCT Filed: Oct. 11, 2010

(86) PCT No.: PCT/IB2010/054599
§ 371 (c)(1),
(2), (4) Date: Apr. 27, 2012

(87) PCT Pub. No.: WO2011/055250
PCT Pub. Date: May 12, 2011

(65) Prior Publication Data
US 2012/0215125 A1  Aug. 23, 2012

Related U.S. Application Data (60) Provisional application No. 61/257,547, filed on Nov. 3, 2009.

(51) Int. Cl.
| | | |
|---|---|---|
| A61B 5/08 | (2006.01) |
| A61B 5/097 | (2006.01) |
| A61M 16/00 | (2006.01) |
| G01N 33/497 | (2006.01) |
| A61M 16/08 | (2006.01) |

(52) U.S. Cl.
CPC ............. *A61M 16/00* (2013.01); *A61B 5/082* (2013.01); *A61B 5/0816* (2013.01); *A61M 16/085* (2014.02); *G01N 33/497* (2013.01); *A61M 2016/0021* (2013.01)

(58) Field of Classification Search
USPC .......................................... 600/532
See application file for complete search history.

(56) References Cited

U.S. PATENT DOCUMENTS

| | | | |
|---|---|---|---|
| 7,556,039 B1 | 7/2009 | Pierrt | |
| 2002/0017300 A1* | 2/2002 | Hickle et al. | 128/204.22 |
| 2004/0149282 A1 | 8/2004 | Hickle | |
| 2004/0210154 A1 | 10/2004 | Kline | |
| 2004/0243016 A1 | 12/2004 | Sanderson | |
| 2005/0121033 A1* | 6/2005 | Starr et al. | 128/204.18 |
| 2007/0277824 A1* | 12/2007 | Aylsworth et al. | 128/204.23 |

(Continued)

FOREIGN PATENT DOCUMENTS

| | | |
|---|---|---|
| EP | 1731188 A2 | 12/2006 |
| EP | 1800705 A2 | 6/2007 |
| EP | 2062531 A1 | 5/2009 |
| JP | 2003299736 A | 10/2003 |

(Continued)

*Primary Examiner* — Michael Kahelin
*Assistant Examiner* — Mitchell E Alter (57) ABSTRACT

Sidestream sampling of gas to determine information related to the composition of gas at or near the airway of a subject is implemented. From such information one or more breathing parameters of subject 12 (e.g., respiratory rate, end-tidal CO2, etc.) are determined, respiratory events (e.g., obstructions, apneas, etc.) are identified, equipment malfunction and/or misuse is identified, and/or functions are performed. To improve the accuracy of one or more of these determinations, information related to pressure at or near the airway of subject is implemented. This information may include detection of pressure at or near a sidestream sampling cell.

18 Claims, 4 Drawing Sheets

(56) References Cited

U.S. PATENT DOCUMENTS

| | | | |
|---|---|---|---|
| 2008/0041172 A1* | 2/2008 | Jaffe et al. | 73/863.83 |
| 2008/0127977 A1 | 6/2008 | Orr | |
| 2009/0118633 A1* | 5/2009 | Jaffe et al. | 600/532 |
| 2010/0147301 A1* | 6/2010 | Kwok | 128/204.21 |
| 2011/0088693 A1* | 4/2011 | Somervell et al. | 128/203.14 |

FOREIGN PATENT DOCUMENTS

| | | |
|---|---|---|
| JP | 2006507905 A | 3/2006 |
| WO | 0195971 A2 | 12/2001 |
| WO | 2004049912 A2 | 6/2004 |
| WO | 2008005907 A2 | 1/2008 |
| WO | 2008091164 A1 | 7/2008 |

* cited by examiner

SYSTEM AND METHOD OF MONITORING BREATHING

BACKGROUND OF THE INVENTION

1. Field of the Invention

The invention relates to monitoring breathing of a subject implementing a sidestream sampling chamber within which the composition of gas is detected.

2. Description of the Related Art

Systems that sample the composition of gas in a breathing circuit in a sidestream configuration are known. Detection of the composition of gas in these system is typically used to determine one or more breathing parameters. However, it is generally believed that information related to pressure or flow within sidestream sampling chambers is not useful in enhancing and/or enabling the determination of breathing parameters, since sidestream chambers are usually pumped to sample gas from the breathing circuit through the chamber.

SUMMARY OF THE INVENTION

One aspect of the invention relates to a system configured to monitor the breathing of a subject. In one embodiment, the system comprises a sample cell, a composition detector, a pressure detector, and one or more processors. The sample cell is in fluid communication with a conduit, wherein the conduit is placed in fluid communication with the airway of the subject by an interface appliance that engages the airway of the subject, and wherein the sample cell is configured to exhaust gas received into the sample cell from the conduit. The composition detector is configured to generate output signals conveying information related to the composition of gas received into the sample cell from the conduit. The pressure detector is configured to generate output signals conveying information related to pressure within the conduit. The one or more processors are configured to execute computer program modules. The one or more computer program modules comprise an interface classification module, and a breathing parameter module. The interface classification module is configured to determine an interface appliance type of the interface appliance based on the output signals generated by the pressure detector. The breathing parameter module is configured to determine one or more breathing parameters based on the output signals generated by the composition detector, and based on the determination by the interface classification module as to the interface appliance type of the interface appliance.

Another aspect of the invention relates to a method of monitoring the breathing of a subject. In one embodiment, the method comprises receiving gas into a sample cell from a conduit, wherein the conduit is placed in fluid communication with the airway of the subject by an interface appliance that engages the airway of the subject; generating output signals conveying information related to the composition of gas received into the sample cell from the conduit; generating output signals conveying information related to pressure within the conduit; executing one or more computer program modules on one or more processors to determine an interface appliance type of the interface appliance based on the output signals conveying information related to pressure within the conduit; and executing one or more computer program modules on one or more processors to determine one or more breathing parameters based on the output signals conveying information related to the composition of gas received into the sample cell from the conduit, and based on the determination of the interface appliance type of the interface appliance.

Yet another aspect of the invention relates to a system configured monitor the breathing of a subject. In one embodiment, the system comprises means for receiving gas into a sample cell from a conduit, wherein the conduit is placed in fluid communication with the airway of the subject by an interface appliance that engages the airway of the subject; means for generating output signals conveying information related to the composition of gas received into the sample cell from the conduit; means for generating output signals conveying information related to pressure within the conduit; means for determining an interface appliance type of the interface appliance based on the output signals conveying information related to pressure within the conduit; and means for determining one or more breathing parameters based on the output signals conveying information related to the composition of gas received into the sample cell from the conduit, and based on the determination of interface appliance type of the interface appliance.

Still another aspect of the invention relates to a system configured to monitor the breathing of a subject. In one embodiment, the system comprises a sample cell, a composition detector, a pressure detector, and one or more processors. The sample cell is in fluid communication with a conduit that communicates with the airway of a subject, and is configured to exhaust gas received into the sample cell from the conduit. The composition detector is configured to generate output signals conveying information related to the composition of gas received into the sample cell from the conduit. The pressure detector is configured to generate output signals conveying information related to pressure within the conduit. The one or more processors are configured to execute computer program modules. The one or more computer program modules comprise a breath identification module and a breathing parameter module. The breath identification module is configured to identify breathing based on the output signals generated by the pressure detector. The breathing parameter module configured to determine one or more breathing parameters based on the output signals generated by the composition detector, and based on the breathing identified by the breath identification module.

Yet still another aspect of the invention relates to a method of monitoring the breathing of a subject. In one embodiment, the method comprises receiving gas into a sample cell from a conduit that communicates with an airway a subject; generating output signals conveying information related to the composition of gas received into the sample cell from the conduit; generating output signals conveying information related to pressure within the conduit; executing one or more computer program modules on one or more processors to identify breathing based on the output signals conveying information related to pressure within the conduit; and executing one or more computer program modules on one or more processors to determine one or more breathing parameters based on the output signals conveying information related to the composition of gas received into the sample cell from the conduit, and based on the identified breathing.

Another aspect of the invention relates to a system configured to monitor the breathing of a subject. In one embodiment, the system comprises means for receiving gas into a sample cell from a conduit that communicates with an airway of a subject; means for generating output signals conveying information related to the composition of gas received into the sample cell from the conduit; means for generating output signals conveying information related to pressure within the conduit; means for identifying breathing based on the output signals conveying information related to pressure within the conduit; and means for determining one or more breathing parameters based on the output signals conveying information related to the composition of gas received into the sample cell from the conduit, and based on the identified breathing.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
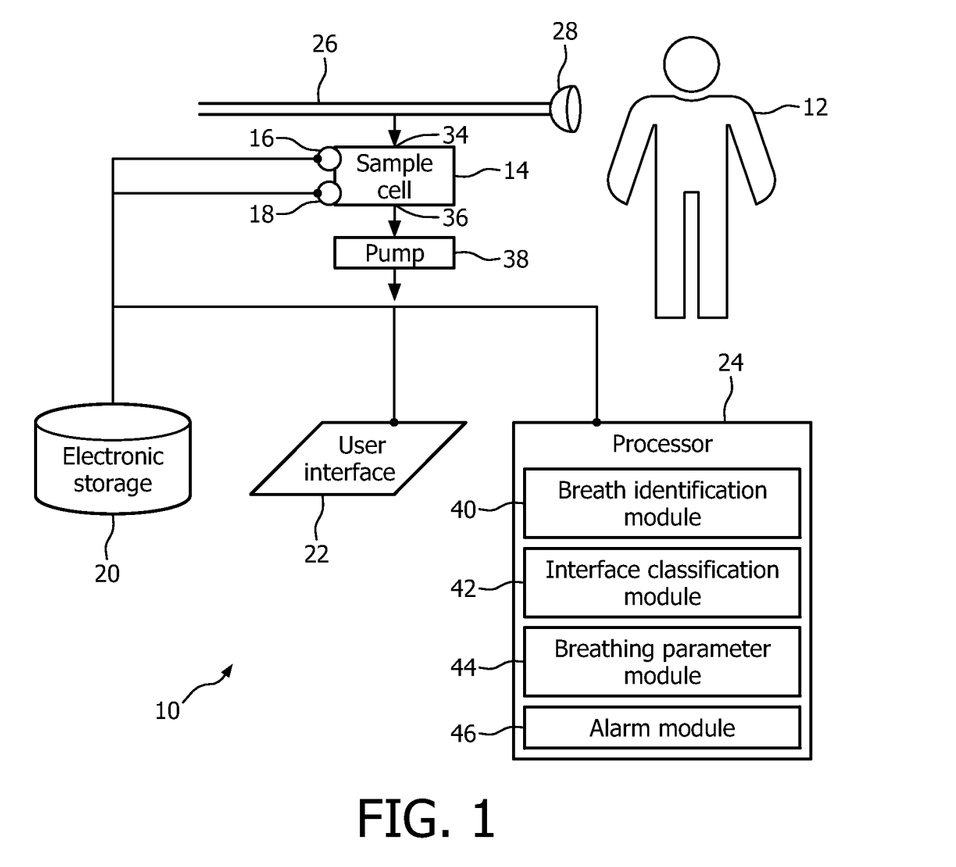
FIG. 1 illustrates a system configured to monitor the breathing of a subject, in accordance with one or more embodiments of the invention.

FIG. 1 illustrates a system 10 configured to monitor the breathing of a subject 12. In one embodiment, system 10 is configured to perform sidestream capnometry to determine information related to the composition of gas at or near the airway of subject 12. Based on such information system 10 determines one or more breathing parameters of subject 12 (e.g., respiratory rate, end-tidal $CO_2$, etc.), identifies respiratory events (e.g., obstructions, apneas, etc.), identifies equipment malfunction and/or misuse, and/or performs other functions. To improve the accuracy of one or more of these determinations, system 10 may further implement information related to pressure at or near the airway of subject 12. In one embodiment, system 10 includes one or more of a sample cell 14, a composition detector 16, a pressure detector 18, electronic storage 20, a user interface 22, one or more processors 24, and/or other components.

In a number of different therapeutic scenarios, an airway of subject 12 is engaged to place a conduit 26 in fluid communication with the airway of subject 12. The airway of subject 12 is engaged, and placed in fluid communication with conduit 26, by an interface appliance 28. The interface appliance 28 may engage one or more orifices of the airway of subject 12 in a sealed or unsealed manner. Some examples of interface appliance 28 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface.

In one embodiment, conduit 26 is configured to deliver a pressurized flow of breathable gas to the airway of subject 12. For example, conduit 26 may be in communication with a pressure generator configured to provide positive pressure support to the airway of subject 12, to mechanically ventilate subject 12, and/or to otherwise provide a pressurized flow of breathable gas to the airway of subject 12. However, this is not intended to be limiting. For example, in one embodiment conduit 26 is in fluid communication with ambient atmosphere As used herein, conduit 26 is not necessarily limited to a tube, or other hollow body, that conveys pressurized gas flows to and/or from interface appliance 28. The conduit 26 may include any hollow body, container, and/or chamber placed in fluid communication with the airway of subject 12 by interface appliance 28. For example, the conduit 26 referred to herein may be formed as a chamber located on the actual interface appliance 28. This chamber may be in fluid communication with a gas source, and/or with ambient atmosphere.

The sample cell 14 is configured to hold gas in isolation from atmosphere, and includes an inlet 34 and an outlet 36. The sample cell 14 is in fluid communication with conduit 26 to receive gas from conduit 26 through inlet 34. Gas is exhausted from sample cell 14 through outlet 36. The gas may be exhausted, for example, to atmosphere, back into conduit 26, and/or otherwise exhausted. In one embodiment, a pump 38 is placed in fluid communication with outlet 36 to draw gas from conduit 26 through sample cell 14.

By virtue of the fluid communication between sample cell 14 and conduit 26 while interface appliance 28 is installed on subject 12, the sample cell 14 holds gas having one or more gas parameters that are the same as, similar to, or impacted by the gas parameters of gas within conduit 26 and/or at the airway of subject 12. For example, the composition of the gas within sample cell 14 is similar to or the same as the gas within conduit 26. Ideally, by virtue of the operation of pump 38 in drawing gas through sample cell 14, the pressure and/or flow of gas within sample cell 14 would remain constant. However, in actuality, the pressure and flow of gas within sample cell 14 fluctuate somewhat with changes in pressure and/or flow within conduit 26. These fluctuations in pressure and/or flow are caused by respiration of subject 12 and the pump. The changes in pressure and/or flow within sample cell 14 caused by respiration of subject 12 are typically much smaller than corresponding changes in pressure and/or flow in conduit 26. Nevertheless, the pressure and/or flow (or parameters related thereto) within sample cell 14 can be used to make inferences about pressure and/or flow within conduit 26, and/or events that cause changes in pressure and/or flow within conduit 26.

As will be appreciated, the illustration of sample cell 14 as being completely separate from conduit 26 (aside from the connection between inlet 34 and conduit 26) is not intended to be limiting. In one embodiment, sample cell 14 is formed within a wall of conduit 26. In one embodiment, sample cell 14 is formed within conduit 26 itself. In one embodiment, sample cell 14 is separate from conduit 26, and the connection between inlet 34 and conduit 26 is formed by a lumen connecting the two.

The composition detector 16 is configured to generate output signals conveying information related to the composition of gas received into sample cell 14 from conduit 26. The information related to the composition of gas may include the concentration of one or more constituent molecular species within the gas received from conduit 26. For example, the output signals generated by composition detector 16 may convey a concentration of carbon dioxide ($CO_2$), oxygen ($O_2$), and/or other molecular species in gas within sample cell 14. The composition detector 16 may include one or more components in direct contact with the gas inside of sample cell 14 (e.g., located within sample cell 14) to detect the information related to the composition of gas in sample cell 14. By way of non-limiting example, the composition detector 16 may include a photoluminescent material disposed in sample cell 14 in direct contact with gas therein.

The pressure detector 18 is configured to generate output signals conveying information related to pressure within conduit 26. In one embodiment, pressure detector 18 includes one or more pressure sensors disposed within sample cell 14, between conduit 26 and sample cell 14, and/or downstream of outlet 36 of sample cell 14. In this embodiment, the output signals generated by pressure detector 18 convey pressure within sample cell 14. As was mentioned above, fluctuations in this pressure may be used to infer pressure changes within conduit 26, and/or to identify events tending to cause pressure changes within conduit 26, such as changes in flow and/or pressure at or near the airway of subject 12.

In one embodiment, a separate spur (not shown) receiving gas from within conduit 26 may be included in system 10. This separate spur and a lumen directing gas from within conduit 26 to inlet 34 may be formed as a dual lumen. The separate spur should be closed (e.g., a "dead end") to pressure detector 18.

In one embodiment, pressure detector 18 includes one or more pressure sensors located in direct contact with gas inside of conduit 26 (e.g., the one or more pressure sensors are disposed within conduit 26). The placement of the one or more pressure sensors in direct contact with the inside of conduit 26 may be selectively removable.

In one embodiment, electronic storage 20 comprises electronic storage media that electronically stores information. The electronically storage media of electronic storage 20 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 20 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 20 may store software algorithms, information determined by processor 24, information received via user interface 22, output signals generated by composition detector 16 and/or pressure detector 18, and/or other information that enables system 10 to function properly. Electronic storage 20 may be a separate component within system 10, or electronic storage 20 may be provided integrally with one or more other components of system 10 (e.g., processor 24).

User interface 22 is configured to provide an interface between system 10 and a user (e.g., subject 12, a caregiver, a researcher, etc.) through which the user may provide information to and receive information from system 10. This enables data, results, and/or instructions and any other communicable items, collectively referred to as "information," to be communicated between the user and system 10. Examples of interface devices suitable for inclusion in user interface 22 include a keypad, buttons, switches, a keyboard, knobs, levers, a display screen, a touch screen, speakers, a microphone, an indicator light, an audible alarm, and a printer. In one embodiment, user interface 22 actually includes a plurality of separate interfaces.

It is to be understood that other communication techniques, either hard-wired or wireless, are also contemplated by the present invention as user interface 22. For example, the present invention contemplates that user interface 22 may be integrated with a removable storage interface provided by memory 20. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 include, but are not limited to, an RS-232 port, RF link, an IR link, modem (telephone, cable or other). In short, any technique for communicating information with system 10 is contemplated by the present invention as user interface 22.

The one or more processors 24 are configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device, or processor 24 may represent processing functionality of a plurality of devices operating in coordination.

As is shown in FIG. 1, processor 24 may be configured to execute one or more computer program modules. The one or more computer program modules may include one or more of a breath identification module 40, an interface classification module 42, a breathing parameter module 44, an alarm module 46, and/or other modules. Processor 24 may be configured to execute modules 40, 42, 44, and/or 46 by software; hardware; firmware; some combination of software, hardware, and/or firmware; and/or other mechanisms for configuring processing capabilities on processor 24.

It should be appreciated that although modules 40, 42, 44, and 46 are illustrated in FIG. 1 as being co-located within a single processing unit, in implementations in which processor 24 includes multiple processing units, one or more of modules 40, 42, 44, and/or 46 may be located remotely from the other modules. The description of the functionality provided by the different modules 40, 42, 44, and/or 46 described below is for illustrative purposes, and is not intended to be limiting, as any of modules 40, 42, 44, and/or 46 may provide more or less functionality than is described. For example, one or more of modules 40, 42, 44, and/or 46 may be eliminated, and some or all of its functionality may be provided by other ones of modules 40, 42, 44, and/or 46. As another example, processor 24 may be configured to execute one or more additional modules that may perform some or all of the functionality attributed below to one of modules 40, 42, 44, and/or 46.

The breath identification module 40 is configured to identify breathing of subject 12 (e.g., breathing transitions, the presence of respiration, etc.). The identification of breathing of subject 12 may be based on the output signals generated by pressure detector 18.

In one embodiment, pressure detector 18 includes one or more pressure sensors actually located inside of sample cell 14. As was mentioned above, fluctuations in pressure within conduit 26 cause corresponding fluctuations in pressure within sample cell 14. Although the fluctuations in pressure within sample cell 14 may be smaller than those within conduit 26, the fluctuations within sample cell 14 may still provide some basis for identifying breathing that causes pressure to change within conduit 26. By way of non-limiting example, general trends the amount of fluctuation may indicate that subject 12 is currently breathing. As another example, drops in pressure indicated in the output signals of pressure detector 18 may be implemented to identify transitions in breathing from exhale to inhale. Similarly, rises in pressure may be implemented to identify transitions in breathing from inhale to exhale.

In one embodiment, pressure detector 18 includes pressure sensors located both between conduit 26 and inlet 34, and upstream of outlet 36 (e.g., between outlet 36 and pump 38). In this embodiment, breath identification module 40 implements the pressure differential between these to positions in the flow path including sample cell 14. When pressure within conduit 26 increases (e.g., during a transition from inhale to exhale), the pressure differential will tend to decrease. By contrast, when pressure within conduit decreases (e.g., during a transition from exhale to inhale), the pressure differential will increase. By monitoring this pressure differential (from the output signals generated by pressure detector 18), breath identification module 40 can identify breathing by subject 12.

In one embodiment, rather than placing the pressure sensors of pressure detector 18 on opposite sides of sample cell 14, a flow restriction (not shown) is placed between conduit 26 and/or inlet 34 of sample cell 14 with a pressure sensor disposed on either side of the flow restriction. The pressure differential between the locations on either side of the flow restriction will tend to vary with pressure inside of conduit 26 in a manner that is similar to pressure differential described above. In this embodiment, breath identification module 40 monitors the pressure differential (from the output signals generated by pressure detector 18) between the two side of the flow restriction to identify transitions in the breathing of subject 12.

It will be appreciated that the pressure differentials described above are not intended to be limiting (e.g., across sample cell 14 and/or across a flow restriction). Pressure detector 18 may include two or more pressure sensors disposed at any combination of locations within the flow path include sample cell 14 (or within a parallel spur from conduit 26) between which a flow of gas causes a different in pressure.

Figure 2:
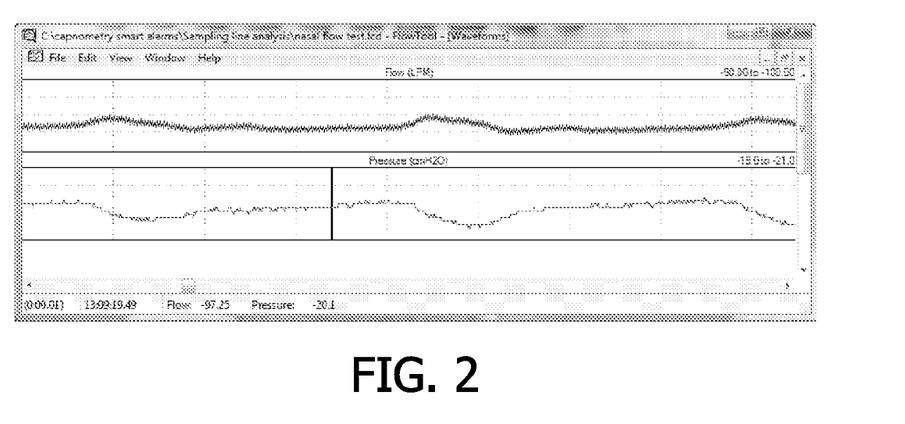
FIG. 2 illustrates plots of pressure and flow in a sidestream sampling chamber, according to one or more embodiments of the invention.

FIG. 2 is a plot of the output signals of a pressure detector similar to or the same as pressure detector 18 (shown in FIG. 1 and described above). As can be seen in FIG. 2, the fluctuations in pressure detected by pressure detector 18 do allow for the identification of breathing, and may even allow for the identification of individual breathing transitions. In the embodiment illustrated in FIG. 2, the pressure detector may include one or more sensors that generate output signals related to the flow of gas through a sample cell. This flow also shows fluctuation with the breathing of a subject through a nasal cannula.

Figure 3:
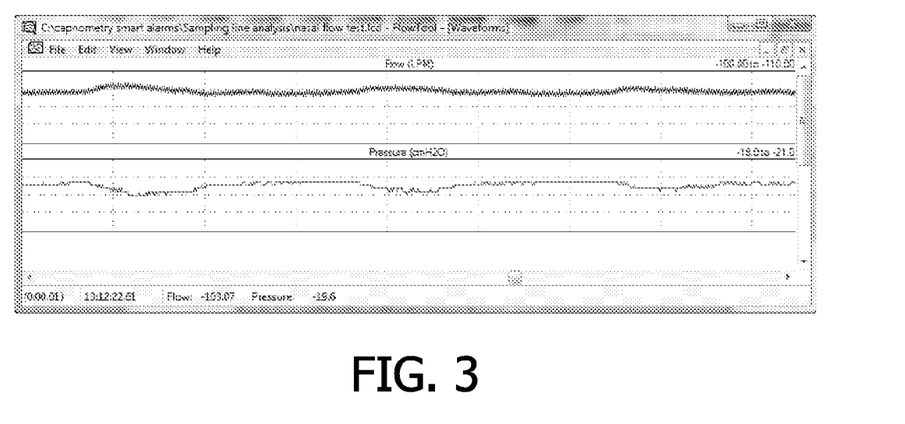
FIG. 3 illustrates plots of pressure and flow in a sidestream sampling chamber, according to one or more embodiments of the invention.

The operation of system 10 shown in FIG. 1 and described above to detect breathing transitions not only works in embodiments in which gas is communicated with the airway of the subject through a "sealed" interface (e.g., intubation, a fully sealed mask, etc.). For example, FIG. 3 is a plot of the output signals of a pressure detector similar to or the same as pressure detector 18 (shown in FIG. 1 and described above) in an embodiment in which gas is communicated with the airway of the subject through a nasal cannula with the subject being able to breathe freely through the mouth and nose.

Returning to FIG. 1, the pump 38 may operate to sample gas through sample cell 14 in pulses. In one embodiment, pump 38 includes a diaphragm pump controlled using pulse width modulation (PWM). These pulses may occur in accordance with the pump motor cycle. This operation of pump 38 may cause noise in the output signals generated by pressure detector 18 by causing fluctuations in pressure at the pulses of pump 38 (e.g., such fluctuations may be observed in the plots shown in FIGS. 2 and 3). In order to reduce this noise, the output signals generated by pressure detector 18 may be sampled and/or filtered at a rate or frequency that corresponds to the pump motor cycle.

In addition to implementing the output signals of pressure detector 18 to identify breathing, breath identification module 40 may further base the identification of breathing on the output signals generated by composition detector 16. As subject 12 breathes, exhalation of subject 12 into interface appliance 28 causes increases in the concentration of some molecular components within conduit 26 and decreases in the concentration of other molecular components within conduit 26 (e.g., $CO_2$ increases and $O_2$ decreases). Similarly, inhalation by subject 12 causes increases in some concentrations and decreases in others.

The interface classification module 42 is configured to determine a type of interface appliance 28 being implemented. During use of an interface appliance 28 that creates a sealed engagement with the airway of subject 12 (e.g., intubation, sealed mask, etc.), the pressure fluctuations within conduit 26 tend to be larger and/or more dramatic than implementations in which the communication of gas between conduit 26 and the airway of the subject is accomplished through an interface appliance 28 that allows leakage, and/or permits free breathing through one or more airway orifices (e.g., nasal cannula).

Figure 4:
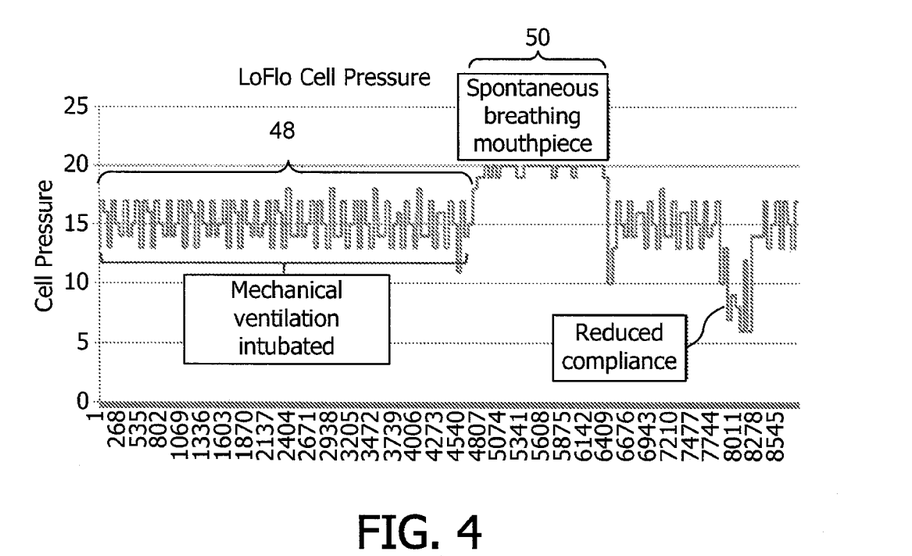
FIG. 4 illustrates plots of sample cell pressure during mechanical and spontaneous ventilation, in accordance with one or more embodiments of the invention.

By way of illustration, FIG. 4 is a plot of pressure that shows how the type of subject interface impacts the magnitude of pressure fluctuations experienced by conduit 26 and/or sample cell 14. During a first period of time 48, the subject is intubated with the airway substantially sealed. During a second period of time 50, the subject is breathing through a nasal cannula, which does not seal the airway. As can be seen from FIG. 4, during the first period of time 48, pressure fluctuations caused by ventilation/respiration have a greater magnitude than during the second period of time 50. From this difference in magnitude, an interface classification module the same as or similar to interface classification module 48 (shown in FIG. 1 and described above) would detect that the airway of the subject was engaged by an interface appliance that seals the airway during the first time period 48 and was breathing through an interface appliance that does not seal the airway during the second time period 50.

In one embodiment, instead of or in addition to monitoring the magnitude of the pressure fluctuations experienced by conduit 26 and/or sample cell 14, the interface classification module monitors a baseline, median, and/or mean pressure. As can be seen in FIG. 4, if the interface appliance being used by the subject seals the airway of the subject, the pressure minima within conduit 26 tend to be lower than the pressure minima experienced with an interface appliance that does not seal the airway of the subject. Based on this difference between the pressure within conduit 26 caused by the different types of interface appliances, the interface appliance module may determine an interface type of the interface appliance being used.

Returning to FIG. 1, breathing parameter module 44 is configured to determine one or more breathing parameters of the breathing of subject 12. The breathing parameter module 44 determines the one or more breathing parameters based on one or more of the output signals generated by composition detector 16, the output signals generated by pressure detector 18, breathing and/or breathing transitions identified by breath identification module 40, determinations by interface classification module 42 of interface appliance classification (e.g., sealed or unsealed), and/or other criteria. The one or more breathing parameters determined by breathing parameter module 44 may include, for example, an end-tidal $CO_2$, a respiratory rate, and/or other breathing parameters.

In determining one of the breathing parameters, the breathing parameter module 44 may determine a breathing parameter as a function of the output signals generated by composition detector 16 and/or the output signals generated by pressure detector 18 based on predetermined relationships between the breathing parameter the output signals generated by composition detector 16 and/or the output signals generated by pressure detector 18. For example, respiratory rate may be determined by breathing parameter module 44 based on a predetermined relationship between the respiratory rate of subject 12 and the output signals generated by composition detector 16. However, the relationship between respiratory rate and the output signals generated by composition detector 16 may be different depending on whether subject 12 is using an interface appliance that seals the airway, or engages the airway without sealing.

Figure 5:
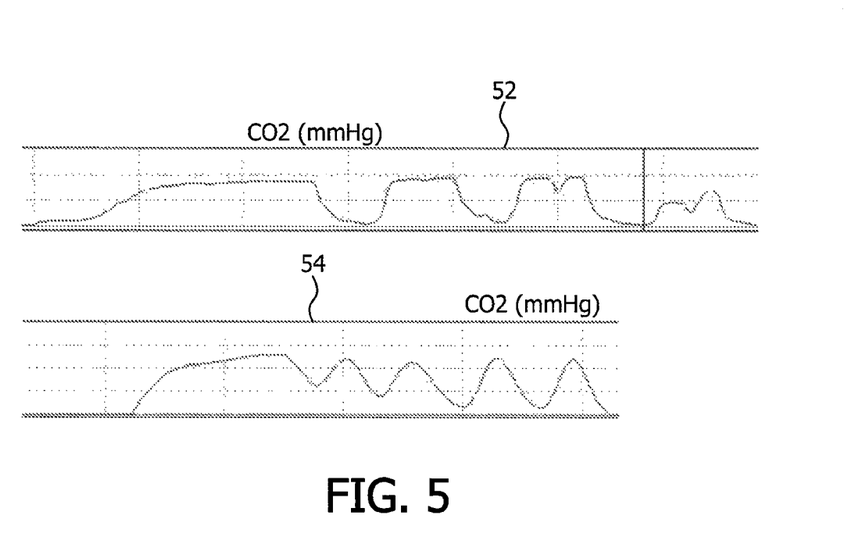
FIG. 5 illustrates plots of CO2 of during mechanical and spontaneous ventilation, in accordance with one or more embodiments of the invention.

By way of non-limiting example, FIG. 5 shows a plot 52 of $CO_2$ at or near the airway of a subject using an interface appliance that does not seal the airway, and a plot 54 of $CO_2$ at or near the airway of a subject using an interface appliance that creates a sealed engagement with the airway. As can be seen in FIG. 5, the relationship between $CO_2$ at or near the airway of 26 and respiratory rate will tend to behave very differently in these two circumstances. As such, calculation of respiratory rate may suffer if a single function describing respiratory rate as a function of the output signals generated by a composition detector is used regardless what type of interface appliance is being implemented.

Returning to FIG. 1, in one embodiment, breathing parameter module 44 is configured to determine one or more breathing parameters of subject 12 by implementing a first set of relationships between the one or more breathing parameters and the output signals generated by composition detector 16 and/or pressure detector 18 if interface classification module 42 determines that interface appliance 28 does not create a sealed engagement with the airway of subject 12. In this embodiment, responsive to interface classification module 42 determining that interface appliance 28 does create a sealed engagement with the airway of subject 12, breathing parameter module 44 implements a second set of relationships between the one or more breathing parameters and the output signals generated by composition detector 16 and/or pressure detector 18 that are tailored to interface appliance 28.

By way of non-limiting example, if interface classification module 42 determines that interface appliance 28 does not seal the airway of subject 12, breathing parameter module 44 implements a first algorithm (based on a first predetermined relationship) to determine end-tidal $CO_2$ as a function of the output signals generated by composition detector 16. However, if interface classification module 42 determines that interface appliance 28 creates a seal with the airway of subject 12, breathing parameter module 44 implements a second algorithm (based on a second predetermined relationship) to determine end-tidal $CO_2$ as a function of the output signals generated by composition detector 16.

In one embodiment, interface classification module 42 may distinguish between different types of interface appliances that do not create a sealed engagement with the airway of subject 12. By way of non-limiting example, interface classification module 42 may distinguish between a nasal cannula and a non-invasive ventilation mask. In this embodiment, breathing parameter module 44 may implement different sets of relationships between the one or more breathing parameters and the output signals generated by composition detector 16 and/or pressure detector 18 that are tailored to the various types of interface appliances that interface classification module 42 is capable of detecting.

The alarm module 46 is configured to generate one or more alarms indicating a respiratory event and/or equipment malfunction. The alarms are communicated to one or more users via user interface 22. Respiratory events and/or equipment malfunctions causing alarm module 46 to generate the one or more alarms are identified based on the output signals generated by composition detector 16 and/or pressure detector 18. By way of non-limiting example, Table 1 below illustrates the manner in which signals generated by composition detector 16 and pressure detector 18 can be implemented to trigger alarms related to respiratory events and/or equipment malfunctions in the event that the interface appliance 28 is a nasal cannula.

(1)

| Signals Generated By Composition Detector Indicate Fluctuations In Composition | Signals Generated By Pressure Detector Indicate Fluctuations In Pressure | Alarm Status |
| --- | --- | --- |
| Present | Present | 1. Breath is valid, 2. etCO2 is reliable 3. Interface appliance is in place in the nares or near mouth |
| Present | Absent | 1. If composition fluctuations indicate high respiration rate, consider cardiogenic oscillations. |

-continued

| Signals Generated By Composition Detector Indicate Fluctuations In Composition | Signals Generated By Pressure Detector Indicate Fluctuations In Pressure | Alarm Status |
|---|---|---|
| Absent | Present | 2. If composition fluctuations indicate normal respiration rate, consider airway obstruction.<br>3. In any case, etCO2 measurement is unreliable.<br>4. If change in pressure variation is sudden, assume sampling cannula is partially dislodged this should be a rare condition<br>1. Cardiac arrest and manual ventilation(bagging)<br>2. Possible obstruction on expiration.<br>3. Composition Detector failure |
| Absent | Absent | 1. Apnea,<br>2. Interface Appliance has been completely removed |

Figure 6:
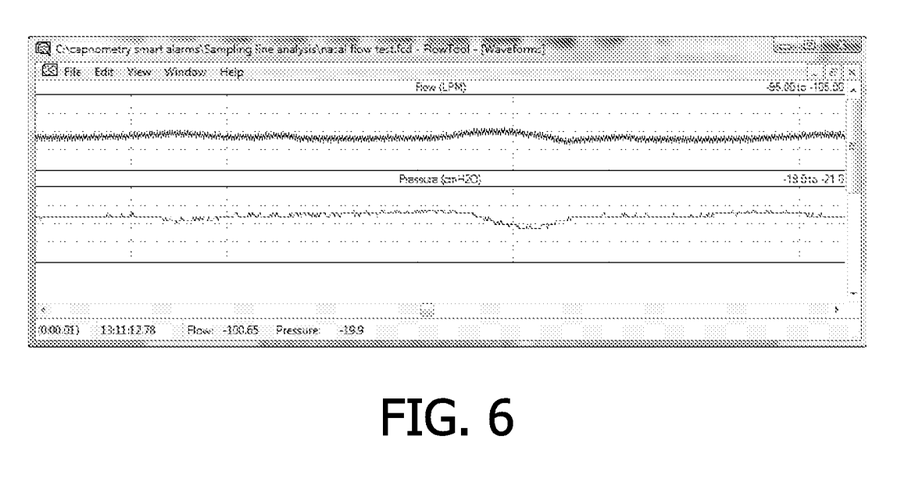
FIG. 6 illustrates plots of pressure and flow in a sidestream sampling chamber, according to one or more embodiments of the invention.

By way of further illustration of the manner in which output signals of pressure detector 18 indicate triggering events for alarms, FIG. 6 shows plots of pressure and flow within a sampling chamber during two successive breaths by a subject. In the first breath a subject interface appliance is mis-installed on a subject, and in the second breath, the subject interface appliance is installed correctly. As will be appreciated from the plots shown in FIG. 6, the mis-installation causes the magnitude and/or frequency of changes in pressure and/or flow within the sampling chamber to drop. Based on a detection that the magnitude and/or frequency of changes in pressure and/or flow had dropped from a level similar to that shown in the plots of either FIG. 2 or FIG. 3 to the level shown in FIG. 6, an alarm module similar to or the same as alarm module 46 may generate an alarm indicating an equipment malfunction (e.g., due to mis-installation) or a respiratory event (e.g., an obstruction).

In one embodiment, processor 24 implements the output of pressure detector 18 alone in combination with any or all of the outputs of the breath identification module 40, interface classification module 42 and breathing parameter module 44 to control pump 38. This is desirable if any portions of the path between interface appliance 28 and sample cell 14 is separable. For example, inlet 34 of sample cell 14 may be disconnected from conduit 26. These outputs of pressure detector 18, breath identification module 40, interface classification module 42, and/or breathing parameter module 44 may be implemented as inputs to a rules engine within processor 24, filters within processor 24, and/or other processing mechanisms configured to detect separation and/or disconnection of the flow path between interface appliance 28 and sample cell 14.

In one embodiment, processor 24 controls pump 38 to enhance detections of pressure fluctuations from signals of pressure detector 18 (e.g., pressure detection may be more reliable without the draw from pump 38). In one embodiment, processor 24 controls pump 38 to reduce the power drawn by pump 38 during operation (e.g., in a battery operated embodiment). Other reasons for controlling pump 38 in accordance with the output signals generated by 18 are also contemplated.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to monitor the breathing of a subject, the system comprising:
   a sample cell in fluid communication with a conduit that communicates with an airway of the subject, wherein the conduit is placed in fluid communication with the airway of the subject by an interface appliance that engages the airway of the subject, wherein the sample cell is configured to exhaust gas received into the sample cell from the conduit;
   a composition detector configured to generate output signals conveying information related to composition of the gas received into the sample cell from the conduit;
   a pressure detector configured to generate output signals conveying information related to pressure within the conduit;
   computer program modules that comprise:
      a breath identification module configured to identify breathing based on the output signals generated by the pressure detector;
      an interface classification module configured to perform a determination of an interface appliance type of the interface appliance based on the output signals generated by the pressure detector; and
      a breathing parameter module configured to determine one or more breathing parameters (i) based on the output signals generated by the composition detector, and (ii) based on one of (ii.a) the breathing identified by the breath identification module and (ii.b) the determination by the interface classification module as to the interface appliance type of the interface appliance; and
   one or more processors configured to execute the computer program modules,
   wherein the interface classification module is configured to determine the interface appliance type from sizes of pressure variations conveyed by the output signals generated by the pressure detector.

2. The system of claim 1, wherein the breath identification module is configured to identify the breathing further based on the output signals generated by the composition detector.

3. The system of claim 1, wherein the one or more breathing parameters comprise at least one of a respiratory rate and end-tidal $CO_2$.

4. The system of claim 1, wherein the computer program modules further comprise an alarm module configured to generate one or more alarms indicating at least one of a respiratory event and an equipment malfunction based on the output signals generated by the composition detector and the pressure detector.

5. The system of claim 1, wherein identifications of the breathing by the breath identification module comprise identifications of breathing transitions, and wherein the breathing parameter module is further configured to determine the one or more breathing parameters based on the output signals generated by the composition detector by:

implementing a first set of predetermined relationships between the output signals generated by the composition detector and the one or more breathing parameters, responsive to a determination by the interface classification module that the interface appliance creates a sealed engagement with the airway of the subject; and implementing a second set of predetermined relationships between the output signals generated by the composition detector and the one or more breathing parameters, responsive to a determination by the interface classification module that an engagement between the interface appliance and the airway of the subject is not sealed.

6. A method of monitoring the breathing of a subject, the method comprising acts of:

receiving gas into a sample cell from a conduit that communicates with an airway the subject, wherein the conduit is placed in fluid communication with the airway of the subject by an interface appliance that engages the airway of the subject;

generating output signals conveying information related to composition of the gas received into the sample cell from the conduit;

generating output signals conveying information related to pressure within the conduit;

executing a breath identification module on one or more processors to identify breathing based on the output signals conveying information related to pressure within the conduit;

executing a breathing parameter module on the one or more processors to perform a determination of an interface appliance type of the interface appliance based on the output signals conveying information related to pressure within the conduit; and executing a breathing parameter module on the one or more processors to determine one or more breathing parameters (i) based on the output signals conveying information related to the composition of the gas received into the sample cell from the conduit, and (ii) based on one of (ii.a) the identified breathing and (ii.b) the determined interface appliance type of the interface appliance, wherein the determination of the interface appliance type of the interface appliance is made based on sizes of pressure variations indicated by the output signals conveying information related to pressure within the conduit.

7. The method of claim 6, wherein breathing is identified further based on the output signals conveying information related to the composition of the gas received into the sample cell from the conduit.

8. The method of claim 6, wherein the one or more breathing parameters comprise oat least one of a respiratory rate and end-tidal $CO_2$.

9. The method of claim 6, further comprising executing an alarm module of the one or more processors to generate one or more alarms indicating at least one of a respiratory event and equipment malfunction based on the output signals conveying information related to the composition of the gas received into the sample cell from the conduit and based on the output signals conveying information related to pressure within the conduit.

10. The method of claim 6, wherein the identifying breathing comprises identifying breathing transitions, and wherein the determining the one or more breathing parameters based on the output signals generated by the composition detector comprises acts of:

implementing a first set of predetermined relationships between the output signals generated by the composition detector and the one or more breathing parameters, responsive to a determination that the interface appliance type creates a sealed engagement with the airway of the subject; and implementing a second set of predetermined relationships between the output signals generated by the composition detector and the one or more breathing parameters, responsive to a determination that the interface appliance type creates an engagement between the interface appliance and the airway of the subject that is not sealed.

11. A system configured to monitor the breathing of a subject, the system comprising:

a sample cell in fluid communication with a conduit, wherein the conduit is placed in fluid communication with an airway of the subject by an interface appliance that engages the airway of the subject, and wherein the sample cell is configured to exhaust gas received into the sample cell from the conduit;

a composition detector configured to generate output signals conveying information related to the composition of the gas received into the sample cell from the conduit;

a pressure detector configured to generate output signals conveying information related to pressure within the conduit; and one or more processors configured to execute computer program modules, wherein the one or more computer program modules comprise:

an interface classification module configured to perform a determination of an interface appliance type of the interface appliance based on the output signals generated by the pressure detector; and a breathing parameter module configured to determine one or more breathing parameters based on the output signals generated by the composition detector, and based on the determination by the interface classification module as to the interface appliance type of the interface appliance, wherein the interface classification module is configured to determine the interface appliance type from sizes of pressure variations conveyed by the output signals generated by the pressure detector.

12. The system of claim 11, wherein the determination of interface appliance type by the interface classification module comprises determining whether or not the interface appliance creates a sealed engagement with the airway of the subject.

13. The system of claim 11, wherein the one or more breathing parameters comprise oat least one of a respiratory rate and end-tidal $CO_2$.

14. The system of claim 12, wherein the breathing parameter module is configured to determine the one or more breathing parameters based on the output signals generated by the composition detector by:

implementing a first set of predetermined relationships between the output signals generated by the composition detector and the one or more breathing parameters, responsive to a determination by the interface classification module that the interface appliance creates the sealed engagement with the airway of the subject; and implementing a second set of predetermined relationships between the output signals generated by the composition detector and the one or more breathing parameters, responsive to a determination by the interface classification module that an engagement between the interface appliance and the airway of the subject is not sealed.

15. A method of monitoring the breathing of a subject, the method comprising:

receiving gas into a sample cell from a conduit, wherein the conduit is placed in fluid communication with an airway of the subject by an interface appliance that engages the airway of the subject;

generating output signals conveying information related to the composition of the gas received into the sample cell from the conduit;

generating output signals conveying information related to pressure within the conduit; and executing one or more computer program modules on one or more processors for a determination of an interface appliance type of the interface appliance based on the output signals conveying information related to pressure within the conduit; and executing one or more computer program modules on one or more processors to for a determination of one or more breathing parameters based on the output signals conveying information related to the composition of the gas received into the sample cell from the conduit, and based on the determination of the interface appliance type of the interface appliance, wherein the determination of the interface appliance type of the interface appliance is made based on sizes of pressure variations indicated by the output signals conveying information related to pressure within the conduit.

16. The method of claim 15, wherein determining the interface appliance type comprises determining whether or not the interface appliance creates a sealed engagement with the airway of the subject.

17. The method of claim 15, wherein the one or more breathing parameters comprise at least one of a respiratory rate and end-tidal $CO_2$.

18. The method of claim 16, wherein the determination of the one or more breathing parameters based on the output signals conveying information related to the composition of the gas received into the sample cell from the conduit, and based on the determination of the interface appliance type of the interface appliance comprises:

implementing a first set of predetermined relationships between the output signals conveying information related to the composition of the gas received into the sample cell from the conduit and the one or more breathing parameters, responsive to a determination that the interface appliance creates the sealed engagement with the airway of the subject; and implementing a second set of predetermined relationships between the output signals conveying information related to the composition of the gas received into the sample cell from the conduit and the one or more breathing parameters, responsive to a determination that the interface appliance does not create the sealed engagement with the airway of the subject.

* * * * *